(12) United States Patent
Lippitt et al.

(10) Patent No.: US 6,368,327 B2
(45) Date of Patent: Apr. 9, 2002

(54) MEDICAL DEVICE

(75) Inventors: Raymond F. Lippitt, 8601 Burning Tree Rd., Bethesda, MD (US) 20817; Robert G. Lippitt, 515 Rosewood Dr., Smithfield, NC (US) 27577; Andrew R. Leopold, Lake Zurich, IL (US)

(73) Assignees: Raymond F. Lippitt, Bethesda, MD (US); Robert G. Lippitt, Smithfield, NC (US)

( * ) Notice: Subject to any disclaimer, the term of this patent is extended or adjusted under 35 U.S.C. 154(b) by 0 days.

(21) Appl. No.: 09/745,180

(22) Filed: Dec. 22, 2000

Related U.S. Application Data

(63) Continuation-in-part of application No. 09/429,950, filed on Oct. 29, 1999, now abandoned, which is a continuation-in-part of application No. 09/317,131, filed on May 24, 1999, now abandoned, which is a continuation-in-part of application No. 09/069,159, filed on Apr. 29, 1998, now Pat. No. 5,906,622, said application No. 09/317,131, is a continuation-in-part of application No. 09/069,160, filed on Apr. 29, 1998, now Pat. No. 5,924,175.

(60) Provisional application No. 60/045,068, filed on Apr. 29, 1997, provisional application No. 60/045,068, filed on Apr. 29, 1997, provisional application No. 60/045,322, filed on May 1, 1997, provisional application No. 60/056,507, filed on Aug. 21, 1997, provisional application No. 60/056,533, filed on Aug. 21, 1997, provisional application No. 60/056,527, filed on Aug. 21, 1997, and provisional application No. 60/056,509, filed on Aug. 21, 1997.

(51) Int. Cl.[7] .............................................. A61B 17/28
(52) U.S. Cl. ...................................... 606/110; 606/207
(58) Field of Search ................................ 606/205–210, 606/564, 565, 566, 567, 151, 157, 174

(56) References Cited

U.S. PATENT DOCUMENTS

| 3,503,398 | A | * | 3/1970 | Fogarty et al. ............. 606/206 |
| 5,373,854 | A | | 12/1994 | Kolozsi |
| 5,575,805 | A | | 11/1996 | Li |
| 5,666,965 | A | | 9/1997 | Bales |
| 5,782,747 | A | | 7/1998 | Zimmon |
| 5,906,622 | A | | 5/1999 | Lippitt |
| 5,924,175 | A | | 7/1999 | Lippitt |
| 6,129,683 | A | * | 10/2000 | Sutton et al. ............... 606/207 |

\* cited by examiner

*Primary Examiner*—Kevin Truong
(74) *Attorney, Agent, or Firm*—Raymond F. Lippitt

(57) ABSTRACT

A medical device comprising a canula assembly having a movable medical instrument assembly on the distal end thereof and a moving assembly on the proximal end thereof. The medical instrument assembly comprises a plurality of cooperating medical instrument structures having proximal ends confined peripherally at a position of confinement and distal ends movable toward and away from each other. Each cooperating medical instrument structure include a longitudinally stable tubular portion at the proximal confined end thereof having an open end spaced from the position of confinement. Each tubular portion has a movable elongated flexure element extending therethrough having a distal end disposed outwardly of the open end of the tubular portion and fixed with respect to a cooperating medical instrument structure at a position thereon spaced from the confined proximal end thereof. The moving assembly includes fixed structure having moving structure movably mounted thereon positioned and configured to be manually moved to effect movement of the distal ends of the movable medical instrument structure by the movement of the movable flexible elements.

14 Claims, 5 Drawing Sheets

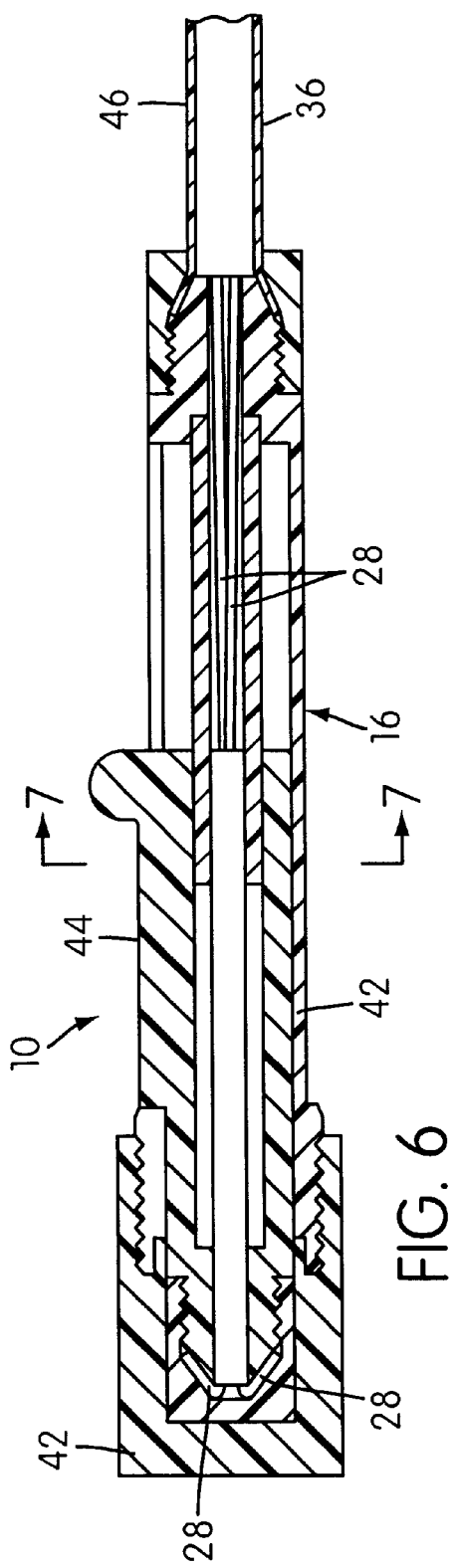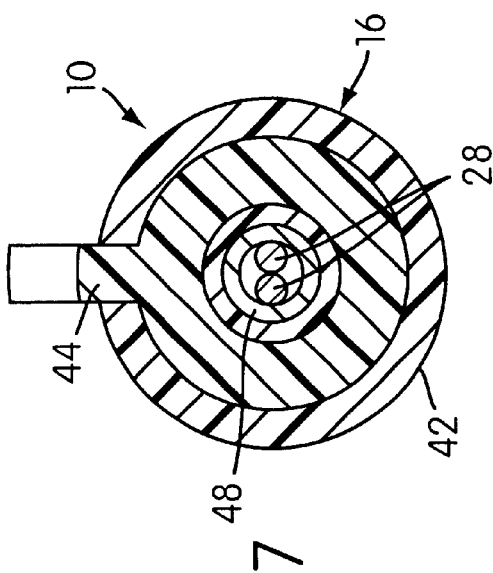

MEDICAL DEVICE

This application is a continuation-in-part of U.S. patent application Ser. No. 09/429,950, filed Oct. 29, 1999, now abandoned which, in turn, is a continuation-in-part of U.S. patent application Ser. No. 09/317,131, filed May 24, 1999, now abandoned which, in turn, is a continuation-in-part of U.S. application Ser. No. 09/069,159, filed Apr. 29, 1998, now U.S. Pat. No. 5,906,622, which claims priority of Provisional Application No. 60/045,068, filed Apr. 29, 1997, Provisional Application No. 60/045,322, filed May 1, 1997, Provisional Application No. 60/056,507, filed Aug. 21, 1997, and Provisional Application No. 60/056,533, filed Aug. 21, 1997. The 09/317,131 application, filed May, 24, 1999 now abandoned is also a continuation-in-part of U.S. patent application Ser. No. 09/069,160, filed Apr. 29, 1998, now U.S. Pat. No. 5,924,175, which claims priority of Provisional Application No. 60/045,068, filed Apr. 29, 1997, Provisional Application No. 60/045,322, filed May 1, 1997, Provisional Application No. 60/056,527, filed Aug. 21, 1997, and Provisional Application No. 60/056,509, filed Aug. 21, 1997, the disclosure of each of which is hereby incorporated by reference into the present specification.

BACKGROUND OF THE INVENTION

This application relates to medical devices and more particularly to medical devices which have dimensions small enough to pass through the central passage of a scope.

The type of medical device herein contemplated includes an elongated canula assembly having a distal end which carries a medical instrument with movable parts constructed and arranged to be inserted into a patient and a proximal end which carries a moving assembly constructed and arranged to be retained exteriorly of the patient.

Our issued U.S. Pat. Nos. 5,906,622 and 5,924,175 illustrate medical instruments in the form of an annularly extending and retracting gripping and releasing assembly, as, for example, a kidney stone extractor instrument. The patents disclosed embodiments of a miniature size sufficient to pass through a three French central passage of a scope. The mechanism of the of the instrument includes a plurality of operative elements which are (1) longitudinally fixed and of generally tubular configuration and (2) longitudinally movable and of elongated configuration suitable to move within the tubular configuration of element (1). Each longitudinally fixed tubular element forms a part of one of a plurality of cooperating medical instrument structures which extend from the confined proximal end thereof to a distal end spaced longitudinally outwardly of the proximal end. Each longitudinally movable elongated element is movably disposed within a longitudinally fixed tubular element forming a part of one of the cooperating medical instrument structures and has a distal end disposed (1) outwardly of the distal end of the one longitudinally fixed tubular element and (2) fixed relative to an adjacent one of the plurality of medical instrument structures at a position spaced longitudinally outwardly of the confined proximal end thereof. In the embodiments disclosed in the patents, the cooperating medicate instrument structures constituted three (or more than three) annularly arranged fixed tubular elements so that the movement of the movable elongated elements within the tubular members and their fixture with respect to the adjacent tubular elements resulted in the annular expansion and contraction of the distal ends of the fixed tubular members. A distinct advantage of the arrangement is that both expansion and contraction are effected positively by the movable elongated elements. While all of the illustrated embodiments in the patents include three or more annularly arranged cooperating medical instrument structures, the principle of operation and the advantages of positive expansion and retraction are applicable to medical instruments which simply have two opposed cooperating medical instrument structures.

BRIEF SUMMARY OF THE INVENTION

Accordingly, it is an object of the present invention to provide a medical device comprising an elongated canula assembly having a distal end constructed and arranged to be inserted into a patient and a proximal end constructed and arranged to be retained exteriorly of the patient. The canula assembly has a medical instrument assembly on the distal end thereof and a moving assembly on the proximal end thereof. The medical instrument assembly comprises a plurality of cooperating medical instrument structures having proximal ends confined peripherally at a position of confinement and distal ends movable toward and away from each other. At least one of the cooperating medical instrument structures includes a longitudinally fixed tubular elements fixed at the proximal confined end thereof having a free end spaced from the position of confinement. The tubular element has a movable elongated flexure element extending therethrough having a distal end disposed outwardly of the free end of the fixed tubular element and fixed with respect to a cooperating medical instrument structure at a position thereon spaced from the confined proximal end thereof. The moving assembly includes fixed structure having moving structure movably mounted thereon spaced from the confined proximal end thereof. The moving assembly includes fixed structure having moving structure movably mounted thereon positioned and configured to be manually moved. The canula assembly includes an elongated longitudinally fixed transversely flexible guide structure extending between the fixed structure of the moving assembly and the proximal end of the fixed tubular element and an elongated flexible moving member disposed in movably guided relation to the elongated longitudinally fixed transversely flexible guide structure connected between the movable structure of the moving assembly and the movable flexure element so that when the moving structure is manually moved in one direction the distal ends of the cooperating medical instrument structures are moved away from one another and when the moving structure is manually moved in an opposite direction the distal ends of the cooperating medical instrument structures are moved toward one another.

DESCRIPTION OF THE DRAWINGS

FIG. 6 is a sectional view of the medical device depicted in FIGS. 1–5 showing the moving assembly at the proximal end thereof;

FIG. 7 is an enlarged sectional view taken along the line 7—7 of FIG. 6; and

DETAILED DESCRIPTION OF THE PREFERRED EMBODIMENTS

Figure 1:
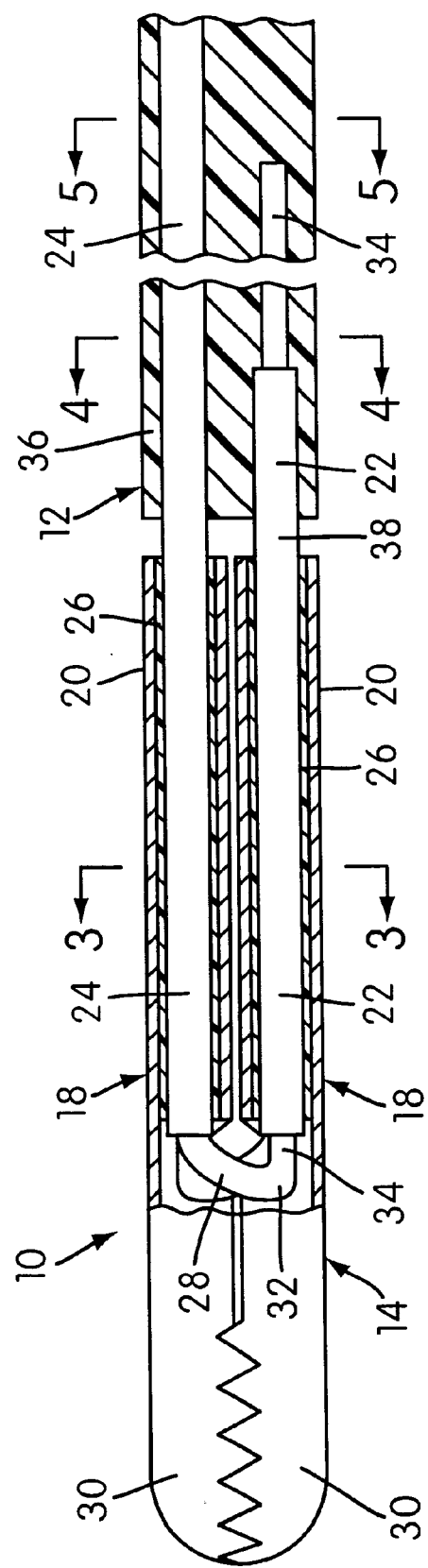
FIG. 1 is a fragmentary side elevational view of a medical device embodying the principles of the present invention, showing the movable medical instrument assembly at the distal end thereof in a fully retracted condition and certain parts in section for purposes of clearer illustration.

Referring now more particularly to FIGS. 1–7 of the drawings, there is shown therein a medical device, generally indicated at 10, embodying the principles of the present invention. The medical device 10 includes an elongated canula assembly, generally indicated at 12, having a movable medical instrument assembly, generally indicated at 14, at a distal end thereof and a moving assembly, generally indicated at 16, at a proximal end thereof. The distal end portion of the canula assembly 12 including the movable medical instrument assembly 14 is constructed and arranged to enter a patient while the proximal end portion of the canula assembly 12 including the moving assembly 16 is constructed and arranged to be retained exteriorly of the patient.

The movable medical instrument assembly 14, as shown, is an endoscopic movable medical instrument assembly, specifically, a biopsy sample taker of the type previously disclosed in U.S. Pat. No. 5,840,143, the disclosure of which is hereby incorporated into the present specification.

The movable medical instrument assembly 14 comprises a plurality of cooperating medical instrument structures, generally indicated at 18, having proximal ends confined peripheral and having distal ends movable toward and away from one another. The medical instrument structures 18 embody a plurality of operating elements. In this embodiment, each of the two medical instrument structures 18 embodies two operating elements now to be described. Each medical instrument structure 18, in the form of a biopsy jaw member, has a tubular portion 20 which forms a part of the operating elements.

Figure 3:
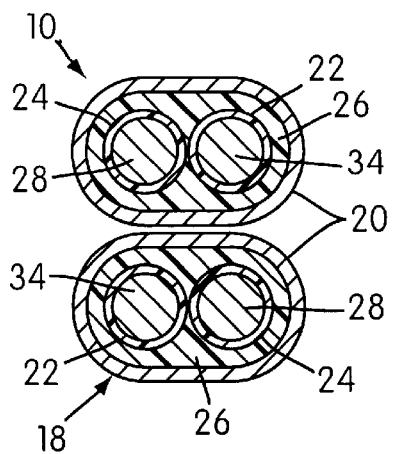
FIG. 3 is an enlarged sectional view taken along the line 3—3 of FIG. 1.
Figure 4:
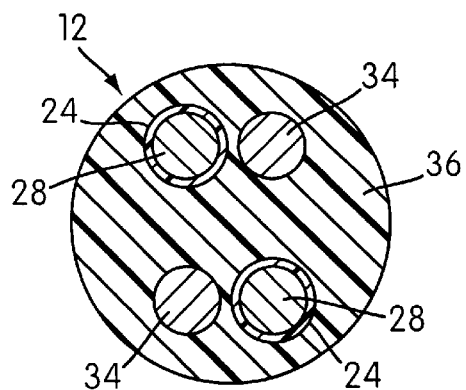
FIG. 4 is a fragmentary sectional view taken along the line 4—4 of FIG. 1.
Figure 5:
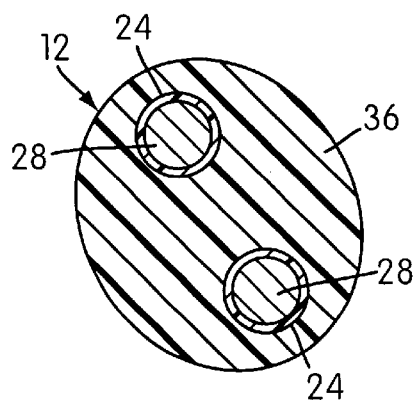
FIG. 5 is an enlarged sectional view taken along the line 5—5 of FIG. 1.

Each tubular portion 20 is formed at a proximal end section thereof and has molded therein a short plastic tube 22 which extends outwardly thereof a short distance and an end portion of a relatively long plastic tube 24. Each of the tubes 22 and 24, as shown in FIG. 3, are disposed in abutting relation with respect to one another within the associated tubular portion 20 and are adhered therein by a thermoplastic molding material 26, such as polyethylene or the like. Each of the tubes 22 and 24 are preferably made of polyimide, although each can be formed of polytetrafluoroethylene (e.g., Teflon® or other suitable material).

The molded in end portion of each long plastic tube 24 forms another part of one of the operating elements. Slidably mounted within each long plastic tube 24 is an elongated wire section 28 constituting a second operating element. Each biopsy taking jaw member 18 is preferably formed from tubular metal stock, as, for example, medical grade stainless steel so that the tubular portion 10 is defined by the stock itself.

Each medical instrument structure 18 also includes a biopsy taking portion 30 at its distal end extending outwardly of the tubular portion 20. As shown, the outer biopsy taking portion 30 is cut along a saw tooth shaped line and then bent outwardly to form spaced side and end biopsy taking surfaces 26.

Each elongated movable wire section 28 has its distal end integrally interconnected, as by a kink 32, with a short fixed wire section 34. As best shown in FIG. 3, each tubular portion 20 is bent inwardly into a generally oval configuration. Each fixed wire section is extended through the short plastic tube 22 in the opposite tubular portion 20 to the one that carries the long plastic tube 24 within which the integral movable wire section 28 extends.

As best shown in FIG. 1, the kinks 32 of the wire sections 28 are disposed outwardly of an adjacent to the distal end of the associated long plastic tube 24 and associated tubular portion 20. Each fixed wire section 30 is long enough so that a free end portion extends somewhat beyond the proximal end of the associated short plastic tube 22 which, in turn, extends somewhat beyond the proximal end of the associated tubular portion 20. Each movable wire section 24 is long enough so that a free end portion thereof extends somewhat beyond the proximal ends of the associated long plastic tube 24 within which it is slidably mounted.

The extending portions of the plastic tubes 22 and 24 and the extending portions of the fixed wire sections 34 form parts of the canula assembly 12. The remainder of the canula assembly 12 is made up of an elongated molded thermoplastic body 36 within which the other parts are embedded. The plastic body 36 is molded by first surrounding the other parts with one or more thermoplastic tubes, as for example a pair of full length plastic tubes surrounding the extensions of each pair of tubes 22 and 24. A single tube surrounding all of the parts or four separate tubes surrounding each of the tubes 22 and 24 could be used. The surrounding tubes are preferably made of low density polyethylene. After the surrounding polyethylene tube or tubes are in place, a full length shrink wrap tube is fed over the surrounding polyethylene tubes. A preferred material for the shrink wrap tube is polytetrafluoroethylene (e.g. Teflon®). Once the shrink wrap tube is in place, the exterior thereof is heated as by a flow of hot air progressively along the entire periphery.

Figure 2:
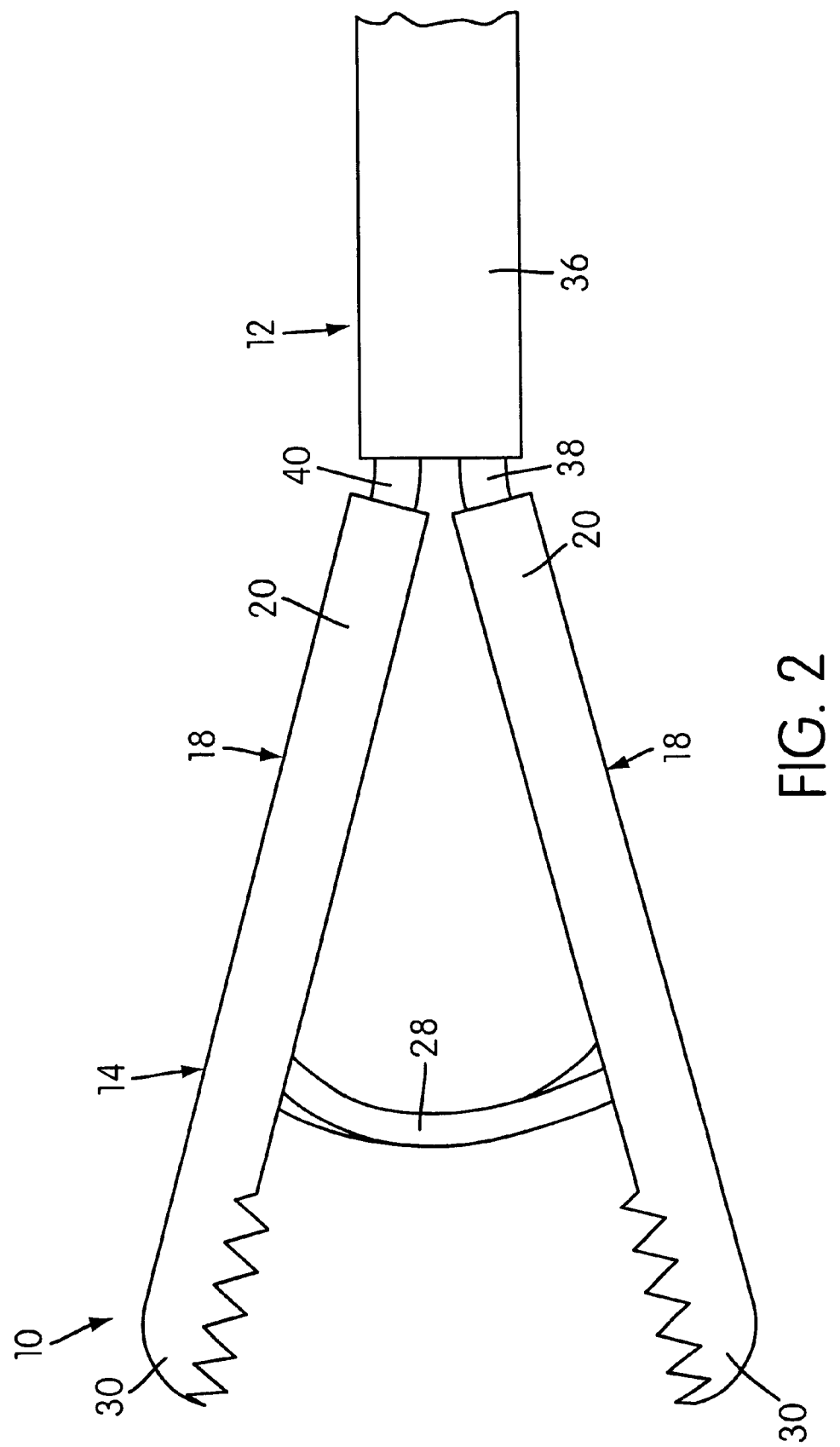
FIG. 2 is a view similar to FIG. 1, showing the movable medical instrument assembly in an expanded condition.

The temperature of the hot air serves to shrink the shrink wrap tube into contact with the polyethylene tubes and to heat the polyethylene to a softening condition so that it flows between any spaces between the polyethylene tubes and the exterior of the polyimide tubes 22 and 24. In this molding process, the softened polyethylene adheres to the extensions of the fixed wire sections 34. Removable spacers may be used in the molding process at the proximal ends of the tubular portions 20 so that short portions 38 and 40 respectively of the tubes 22 and 24 are left between the proximal ends of the tubular portions 20 and the distal end of the polyethylene body 36, as shown in FIGS. 1 and 2. After the longitudinally progressive heating of the exterior of the shrink wrap tube is completed, the shrink wrap tube is longitudinally scored and removed along with the removable spacers.

The resultant canula assembly 12 is thus connected with the cooperating medical instrument structures 18 by the tube portions 38 and 40 and the wire extents therein acting as confining hinges for the proximal end structures 18 and permitting the distal ends thereof to be moved or angularly flexed transversely away from one another into a spaced open position, as shown in FIG. 2.

It is within the broadest aspects of the present invention to fix the fixed wire sections 34 directly to their associated tubular portions 20, as by soldering, brazing or laser welding, so that only two polyimide tube portions 40 and the contained wire extent would form the confining hinge. The use of the short tube portions 38 and contained wire extents are preferred since they provide with the portions 40 and the wire extents confined therein a much more balanced confining hinge effect.

The construction wherein the distal end portions of the tubes 22 and 24 are fixed by molded material to each medical instrument structure 18 provides a longitudinally stable tubular portion in the form of a plastic tube portion 24 at the proximal end portion of each medical instrument structure 18. The provision of the parallel plastic tube portion 42 at the proximal end portion of each medical instrument structure 18 facilitates assembly by enabling each wire to be installed by feeding the long movable wire section 28 through one of the tubes 44 until the integral fixed wire section 34 is reached which can then be fed through the tube 42 of the other structure 18 simultaneously with the completion of the movable wire section 28 feed. The fixed securement of each fixed wire section 34 to its associated medical instrument structure 18 is conveniently accomplished during the molding of the plastic material 36 o the canula assembly 12. The fixing of each fixed wire section 34 establishes the position of the associated kink 32 which determines the fixed position of the distal end of each movable wire section 28. The long plastic tubes 24 which are molded to become fixed parts of both the medical instrument structures 18 and the canula assembly provide slidable control of the movable wire sections 28 substantially throughout their length in addition to providing parts of the hinge connection as aforesaid.

The moving assembly 16, as shown in FIGS. 6 and 7, is constructed in accordance with the disclosure of our aforesaid patents to which reference may be made for a detailed operating description. For present purposes, it is sufficient to note that the moving assembly 16 includes fixed structure 42 constructed and arranged to be manually gripped by the user and moving structure 44 mounted in the fixed structure 42 for manual thumb movement in opposite directions. As shown, the proximal end of the canula assembly 12 has a flexible tubular protector 46 fixed to the exterior of the plastic body 36 which is fixedly secured in the forward end of the fixed structure 42 and serves to fix the proximal ends of the plastic body 36 to the fixed structure 42 of the moving assembly 16.

The proximal ends of the movable wire sections 28 extend rearwardly of the tubes 24 and are anchored within a thin-walled tube 48 fixedly carried by the movable structure 44 of the moving assembly 16.

It can be seen that, by moving the movable structure 44 forwardly, the movable wire sections 28 will be moved forwardly within the tubes 24 which are held stationary so that the distal portions of the wire sections 28 will move out of the distal ends of the tubes 24 and the tubular portions 20 to cause the biopsy surfaces 30 to positively move apart. When the movable structure 42 is moved rearwardly, the movable wire sections 28 will be retracted to move the biopsy surfaces 30 positively together. The manner in which the biopsy surfaces 30 are utilized to take a biopsy in a biopsy taking procedure is the same as described in the aforesaid '043 patent.

In this embodiment, the peripheral confinement and pivot for the pair of cooperating movable biopsy taking instrument structures 18 is provided by the tube portions 38 and 40 and the wire extents contained therein. Providing the pivot for the cooperating movable instrument structures 18 by the wire sections themselves and the tubes which receive them is a desirable feature enabling size to be minimized. Where space permits, it is within the contemplation of the invention that the peripheral confinement and pivoting functions can be provided by separate structure designed to accomplish these functions above. Examples of confining and pivoting structures of this type are disclosed in the following U.S. Pat. Nos. 5,752,973, 5,782,747, 5,908,437, 5,947,984, and 5,954,720, the disclosure of each of which is hereby incorporated by reference into the specification of the present application. These patents also disclose various types of surgical instruments which can be utilized in lieu of the biopsy-taking instrument described above.

Figure 8:
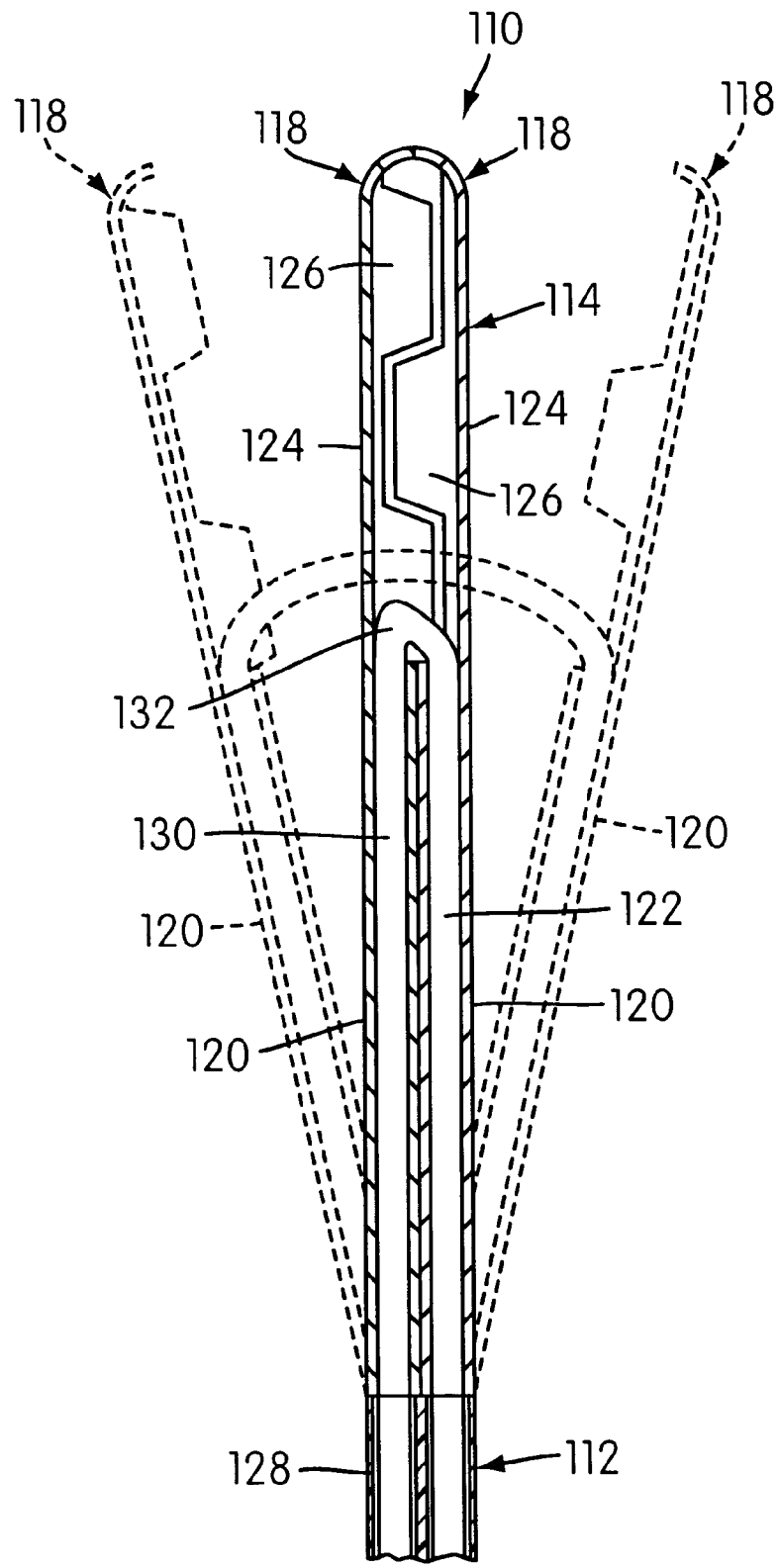
FIG. 8 is a fragmentary side elevational view of another form of medical device embodying the principles of the present invention, showing the movable medical instrument assembly in a fully retracted condition in solid lines and in a fully expanded condition in broken lines.

Referring now more particularly to FIG. 8, there is shown therein another embodiment of a medical device, generally indicated at 110, embodying the principles of the present invention. As before, the medical device 110 includes an elongated canula assembly 112 having a movable medical instrument assembly 114 at its distal end and a moving mechanism such as the moving mechanism 16 previously described at its proximal end.

As shown, the movable medical instrument assembly 14 is in the form of an alligator-type gripping and releasing mechanism which includes two cooperating medical instrument structures, generally indicated at 118. The medical instrument structures 118, as shown in this embodiment, constitutes a pair of cooperating alligator jaw members peripherally confined at a proximal confinement position and having distal portions which are movable toward and away from one another. As before, the medical instrument structures 118 embody a plurality of operating elements. In this embodiment, rather than having two medical instrument structures which embody four operating elements, there are two medical instrument structures 118 which embody essentially only two operating elements. One of the medical instrument structures 118 in the form of an alligator jaw member has a tubular portion 120 at the proximal end section thereof within which an elongated wire section 122 constituting a second operating element is mounted for longitudinal movements in opposite directions. The one alligator jaw member 118 is preferably formed from tubular metal stock, as for example medical grade stainless steel, so that the tubular portion thereof is defined by the stock itself. The medical instrument includes a gripping portion 124 extending outwardly of the tubular portion 120. As shown, the outer gripping portion is cut along a blunt sinusoidal line and then bent outwardly to form spaced side and end grippers 126. Preferably, the other instrument structure 118 is of similar construction simply as a matter of manufacturing convenience. However, the tubular portion 120 of the other instrument structure does not perform the same function of receiving a movable operating element such as the elongated wire section.

The canula assembly 12 between the movable medical instrument assembly 14 at its distal end and the moving assembly 16 at its proximal end includes an elongated longitudinally stable and transversely flexible guide structure in the form of an elongated biluminal plastic tube 128 having its distal end disposed in abutting relation to the proximal ends of the tubular portions of the medical instrument structures 118 and its proximal end fixed to the fixed structure of the moving assembly 16. The movable wire section 122 extends from the proximal end of the tubular portion 120 into and through one lumen of the biluminal tube 128 and having its proximal end fixed to the movable structure 44 of the moving assembly 16.

The distal end of the movable wire section 122 is arranged to be fixed to the other medical instrument structure 18 at a position outwardly of the position of confinement thereof. Preferably, this securement is effected by a fixed wire section 130 integrally interconnected at its distal end with the distal end of the wire section 122, as by a 140° kink 132. The fixed wire section 130 extends within the tubular portion 120 of the other medical instrument structure 118 and beyond into and through the other lumen of the biluminal tube and have its proximal end fixed to the fixed structure 42 of the moving assembly 16.

Preferably, the oppositely facing surfaces of the abutting ends of the biluminal tube 128 and tubular portions 120 are sprayed with an adhesive to provide an additional hinge or pivotal effect to the main pivot for the instrument structures 118 provided by the wire sections extending therebetween one fixed (130) and one movable (122). The alligator jaw members 118 are moved in the same fashion as the biopsy taking jaw members 18.

In the construction of the components thus far described, it is preferable to utilize nitinol as the material for the wire sections with the kink 34 being formed in memory. The tubes are preferably of a medically approved plastic material such as polyethylene, polypropylene, polyester, polyvinyl chloride, polyimide or the like. The adhesive is preferably a medical grade silicone. The other types of medical instrument assemblies that can be utilized as described in the aforesaid patents include surgical clamps, cutters, grippers and the like.

Any U.S. patents or patent applications mentioned or cited hereinabove are hereby incorporated by reference into the present application.

It will thus be seen that the objects of this invention have been fully and effectively accomplished. It will be realized, however, that the foregoing preferred specific embodiments have been shown and described for the purpose of illustrating the functional and structural principles of this invention and are subject to change without departure from such principles. Therefore, this invention includes all modifications encompassed within the spirit and scope of the following claims.

What is claimed is:

1. A medical device comprising an elongated canula assembly having a movable medical instrument assembly on a distal end thereof constructed and arranged to enter the human body to perform a specific procedure, and a moving assembly on a proximal end thereof constructed and arranged to be manually operated outside the human body to move the movable medical instrument assembly during the performance of the procedure, said medical instrument assembly comprising a plurality of cooperating medical instrument structures having proximal ends confined peripherally at a position of confinement and distal ends movable toward and away from each other, at least one of said cooperating medical instrument structures including a longitudinally stable tubular portion at the proximal confined end thereof having an open end spaced from said position of confinement, said tubular portions having a movable elongated flexure element extending therethrough having a distal end disposed outwardly of the open end of said tubular portion and fixed with respect to a cooperating medical instrument structure at a position thereon spaced from the confined proximal end thereof, said moving assembly including fixed structure having moving structure movably mounted thereon positioned and configured to be manually moved, said canula assembly including an elongated longitudinally stable transversely flexible guide structure extending between the fixed structure of said moving assembly and the proximal end of said tubular portion and an elongated flexible moving structure disposed in movably guided relation to said elongated longitudinally fixed transversely flexible guide structure connected between the movable structure of said moving assembly and said movable flexure element so that when said moving structure is manually moved in one direction the distal ends of said cooperating medical instrument structures are moved away from one another and when said moving structure is manually moved in an opposite direction the distal ends of said cooperating medical instrument structures are moved toward one another.

2. A medical device as defined in claim 1 wherein said movable flexure element is a movable wire section fixed with respect to a cooperating medical instrument structure by a fixed wire section integrally connected with the distal end thereof by a kink which determines the fixed position of the distal end of said movable wire section.

3. A medical device as defined in claim 2 wherein said movable and fixed wire sections are made of nitinol with said kink being formed in memory.

4. A medical device as defined in claim 3 wherein said medical instrument structures are opposed biopsy taking members.

5. A medical device comprising an elongated canula assembly having a movable medical instrument assembly on a distal end thereof constructed and arranged to enter the human body to perform a specific procedure, and a moving assembly on a proximal end thereof constructed and arranged to be manually operated outside the human body to move the movable medical instrument assembly during the performance of the procedure, said medical instrument assembly comprising a plurality of cooperating medical instrument structures having proximal ends confined peripherally at a position of confinement and distal ends movable toward and away from each other, each of said cooperating medical instrument structures including a longitudinally stable tubular portion at the proximal confined end thereof having an open end spaced from said position of confinement, each of said tubular portions having a movable elongated flexure element extending therethrough having a distal end disposed outwardly of the open end of said tubular portion and fixed with respect to a cooperating medical instrument structure at a position thereon spaced from the confined proximal end thereof, said moving assembly including fixed structure having moving structure movably mounted thereon positioned and configured to be manually moved, said canula assembly including an elongated longitudinally stable transversely flexible guide structure extending between the fixed structure of said moving assembly and the proximal end of said tubular portion and an elongated flexible moving structure disposed in movably guided relation to said elongated longitudinally fixed transversely flexible guide structure connected between the movable structure of said moving assembly and said movable flexure element so that when said moving structure is manually moved in one direction the distal ends of said cooperating medical instrument structures are moved away from one another and when said moving structure is manually moved in an opposite direction the distal ends of said cooperating medical instrument structures are moved toward one another.

6. A medical device as defined in claim 5 wherein each of said movable flexure elements is a movable wire section fixed with respect to a cooperating medical instrument structure by a fixed wire section integrally connected with the distal end thereof by a kink which determines the fixed position of the distal end of said movable wire section.

7. A medical device as defined in claim 6 wherein said tubular portion includes a distal end portion of an elongated plastic tube having a proximal portion which extends completely through said canula assembly.

8. A medical device as defined in claim 7 wherein each medical instrument structure includes a distal end portion of a short plastic tube disposed in parallel relation to the distal end portion of said elongated plastic tube, each short plastic tube including a proximal end portion extending into said canula assembly, each fixed wire section extending through an associated short plastic tube and having a proximal end portion extending into said canula assembly, said canula assembly including an elongated body of thermoplastic material adhered to the exterior wire section and the peripheries of the proximal end portions of said fixed peripheries of the proximal end portions of said plastic tubes so as to leave short portions thereof extending between proximal ends of said medical instrument structures and a distal end of said body of thermoplastic material which together with the wire extents therein serve as confining hinges for said medical instrument structures.

9. A medical device as defined in claim 8 wherein said movable and fixed wire sections are made of nitinol with said kink being formed in memory.

10. A medical device as defined in claim 9 wherein said plastic tubes are formed of polyimide.

11. A medical device as defined in claim 10 wherein said body of thermoplastic material is polyethylene.

12. A medical device as defined in claim 11 wherein said medical instrument structures are opposed biopsy taking members.

13. A medical device as defined in claim 6 wherein said movable and fixed wire sections are made of nitinol with said kink being formed in memory.

14. A medical device as defined in claim 5 wherein said medical instrument structures are opposed biopsy taking members.

* * * * *